United States Patent [19]

Delony et al.

[11] Patent Number: 4,574,040
[45] Date of Patent: Mar. 4, 1986

[54] APPARATUS FOR VERTICAL GEL ELECTROPHORESIS

[75] Inventors: Timothy E. Delony, San Leandro; Daniel Y. M. Chu, San Francisco, both of Calif.

[73] Assignee: Bio-Rad Laboratories, Inc., Richmond, Calif.

[21] Appl. No.: 655,001

[22] Filed: Sep. 26, 1984

Related U.S. Application Data

[63] Continuation-in-part of Ser. No. 601,193, Apr. 17, 1984, abandoned.

[51] Int. Cl.[4] .............................................. G01N 27/28
[52] U.S. Cl. ................................. 204/299 R; 204/182.8
[58] Field of Search ........................ 204/299 R, 180 G

[56] References Cited

U.S. PATENT DOCUMENTS

| | | | |
|---|---|---|---|
| 3,902,986 | 9/1975 | Nees | 204/299 |
| 3,932,265 | 1/1976 | Hoefer | 204/299 |
| 3,980,540 | 9/1976 | Hoefer | 204/180 |
| 4,224,134 | 9/1980 | Hoefer et al. | 204/299 |
| 4,284,491 | 8/1981 | Vesterberg | 204/180 G |
| 4,292,161 | 9/1981 | Hoefer et al. | 204/299 |
| 4,325,796 | 4/1982 | Hoefer et al. | 204/299 R |
| 4,518,476 | 5/1985 | Delony et al. | 204/299 R |

OTHER PUBLICATIONS

F. W. Studier, "Analysis of Bacteriophage T7 Early RNAs and Proteins on Slab Gels", *J. Mol. Biol.*, (1973) 79, pp. 237-248.
D. M. Abadi, "Discontinuous Electrophoresis on Polyacrylamide Gel Slab", *Clinical Chemistry*, vol. 15, No. 1, (1969), pp. 35-41.
S. Raymond, "A Convenient Apparatus for Vertical Gel Electrophoresis", *Clinical Chemistry*, vol. 8, No. 5, (1962), pp. 455-470.
R. O. Poyton, "A Versatile Apparatus for Polyacrylamide and Agarose Gel Electrophoresis in Plexiglas Slab Gel Molds", *Analytical Biochemistry*, 90, pp. 624-632 (1978).
Hoefer Scientific Instruments, Vertical Slab Polyacrylamide Gel Electrophoresis (no date).
R. M. Roberts et al., "Improved Apparatus for Vertical Gel Electrophoresis", *Analytical Biochemistry*, 49, pp. 592-597 (1972).
A. C. C. Broadmeadow et al., "Polyacrylamide Slab Gel Electrophoresis-An Improved Design", *Analytical Biochemistry*, 100, pp. 87-91 (1979).
M. S. Reid et al., "A Simple Apparatus for Vertical Flat-Sheet Polyacrylamide Gel Electrophoresis", *Analytical Biochemistry*, 22, pp. 374-381 (1968).
Madjar et al., "A Simple Water-Cooled Apparatus for Two-Dimensional Gel Electrophoresis", *Analytical Biochemistry*, 83, (1977), pp. 304-310.
J. A. Rowe, "Apparatus for Routine Vertical Acrylamide Gel Slab Electrophoresis", *Clinica Chimica Acta*, 47 (1973), pp. 63-68.
R. C. Woodworth et al., "An Improved Vertical Polyacrylamide Gel Electrophoresis Apparatus", *Analytical Biochemistry*, 18, pp. 295-304 (1967).

*Primary Examiner*—Andrew H. Metz
*Assistant Examiner*—B. J. Boggs, Jr.
*Attorney, Agent, or Firm*—Townsend and Townsend

[57] ABSTRACT

An electrophoresis cell assembly is disclosed which accommodates one or more vertically oriented gels of either slab or tube geometry held in a lateral enclosure attachable to a U-shaped frame to form a liquid-tight upper buffer chamber surrounding the upper end of the gel. Mated features on the gel enclosure and the frame permit one to slide the enclosure up against the frame into pivotal contact therewith, and to then lock the enclosure into position against the frame, sealing the buffer chamber thus formed around the upper end of the gel, all done in one simple movement. The design overcomes problems in both sealing and assembly, and provides a reliably sealed construction which may be combined with other pieces of equipment normally used in electrophoretic separations to provide a complete cell. The entire construction can be assembled and disassembled with unusual ease.

18 Claims, 11 Drawing Figures

APPARATUS FOR VERTICAL GEL ELECTROPHORESIS

CROSS REFERENCE TO RELATED APPLICATION

This application is a continuation-in-part of co-pending application Ser. No. 601,193, filed Apr. 17, 1984 and now abandoned.

BACKGROUND OF THE INVENTION

This invention relates to apparatus for performing electrophoresis. In particular, this invention relates to an apparatus for supporting a vertical gel or a series of such gels together with the buffer solutions necessary for the electrophoretic separation of samples along the gels in the vertical direction.

Gel electrophoresis is a widely used and highly effective technique for separating complex mixtures of chemical species. It is useful for both analytical and preparatory purposes, and is well-known for its unique ability to separate complex chemical species such as proteins, polypeptides, nucleic acids and oligonucleotides. It receives particularly wide use in the biotechnology industries.

In both tube gels and slab gels, electrophoresis is frequently done with the gel in the vertical or upright position. This facilitates the insertion of samples at one end (the top end of a tube gel or the top edge of a slab gel), and also facilitates the immersion of the top and bottom ends in appropriate buffer solutions.

This arrangement has its problems, however. Since two buffer solutions are involved, they are frequently at different heights and must be sealed off from each other to prevent leakage between themselves. Many cell structures have been designed which prevent such leakage, but are awkward to use. For example, the laboratory technician is normally called upon to cast the gel, then seal it into the cell assembly so that when the buffers are added there is full contact with the edges of the gel yet no leakage, then add the samples, add the buffer solutions, and run the separation, then disassemble the entire apparatus and prepare it for the next run using a newly cast gel and a new set of samples. Each assembly or disassembly step is prone to human error, raising the possibility of leakage, and the overall procedure is complicated and lengthy. In addition, tube gels and slab gels, due to their different geometries, generally required separate pieces of equipment, each designed exclusively for one or the other.

In either type of gel geometry, one of the most critical parts of the procedure in assembling a vertical cell is containing and sealing the upper buffer solution in a manner which will prevent it from leaking down into the lower buffer solution. In sandwich-type slab gel assemblies (in which the gel is cast between two flat plates), this problem is partially solved by using plates of unequal height. The taller plate thus extends above the upper edge of the gel slab and acts as one wall of the chamber which contains the upper buffer solution. Nevertheless, it remains difficult to join the remaining walls of the buffer chamber to the gel plate assembly in a leak-proof manner.

Sandwich-type slab gel assemblies using plates of unequal height present a further sealing problem, i.e., forming lateral seals to enclose the space above the gel. This problem is particularly acute when the plates are designed to be separated and reassembled by the user in between each use. One attempt to overcome this is the use of a notched plate as the shorter plate—i.e., having a single long notch in the center extending for the entire width of the gel, the ends of the plate being the same height as the taller plate. Examples are those supplied by Hoefer Scientific Instruments, San Francisco, Calif., as part of its Vertical Slab Electrophoresis Unit SE-500; and those disclosed by F. W. Studier in "Analysis of Bacteriophage T7 Early RNAs And Protein On Slab Gels," *J. Mol. Biol.*, 79, 237–248 (1973). Since the plates are usually made of glass, however, notched plates are expensive to make and the upward extensions on each side are easily broken.

SUMMARY OF THE INVENTION

The present invention resides in a novel design for a vertical electrophoresis cell which overcomes the problems of the prior art and accommodates either slab gels, tube gels or both. This design enables one to form a liquid-tight buffer chamber at the upper end of the gel by merely sliding the gel enclosure, appropriately shaped to accommodate either tube gels or slab gels, up against a U-shaped frame and locking it into position. The sliding contact is facilitated by pins and cooperating guide slots, one on the gel enclosure and the other on the frame, which bring the gel enclosure and frame into pivotal contact, preferably with the upper end of the gel enclosure in position against the frame in a hinge-type connection. Locking is then achieved by releasable catches which secure the gel enclosure in a fixed position against the frame, using a suitable gasket for liquid-tight contact. The result is an apparatus capable of leak-proof assembly in a reliable and reproducible manner, requiring but one simple movement by the user. Once assembled, the combination of gel enclosure and upper buffer chamber frame can be placed in a container so that the lower edge of the gel is immersed in a separate buffer solution to permit electrophoresis to take place.

The structure is useful for both slab gels and tube gels, and is particularly well adapted for use with sandwich-type gel slab assemblies as described above, where the plates are of unequal height. Preferred embodiments of the apparatus are especially adapted to accommodate slab gel sandwiches where both plates are straight-edged on top rather than one being notched. Additional features which appear in preferred embodiments include a coolant chamber positioned below the U-shaped frame, and a symmetrical construction to accommodate two opposing gel enclosures. Further features of preferred embodiments will be evident from the description which follows.

BRIEF DESCRIPTION OF THE DRAWINGS

FIGS. 3a and 3b illustrate one of the end clamps for the plate assembly shown in both FIGS. 1 and 2.

FIGS. 4a, 4b, and 4c show the U-shaped support frame for the upper buffer chamber, incorporating also a coolant chamber.

DETAILED DESCRIPTION OF THE INVENTION AND PREFERRED EMBODIMENTS

Figure 1:
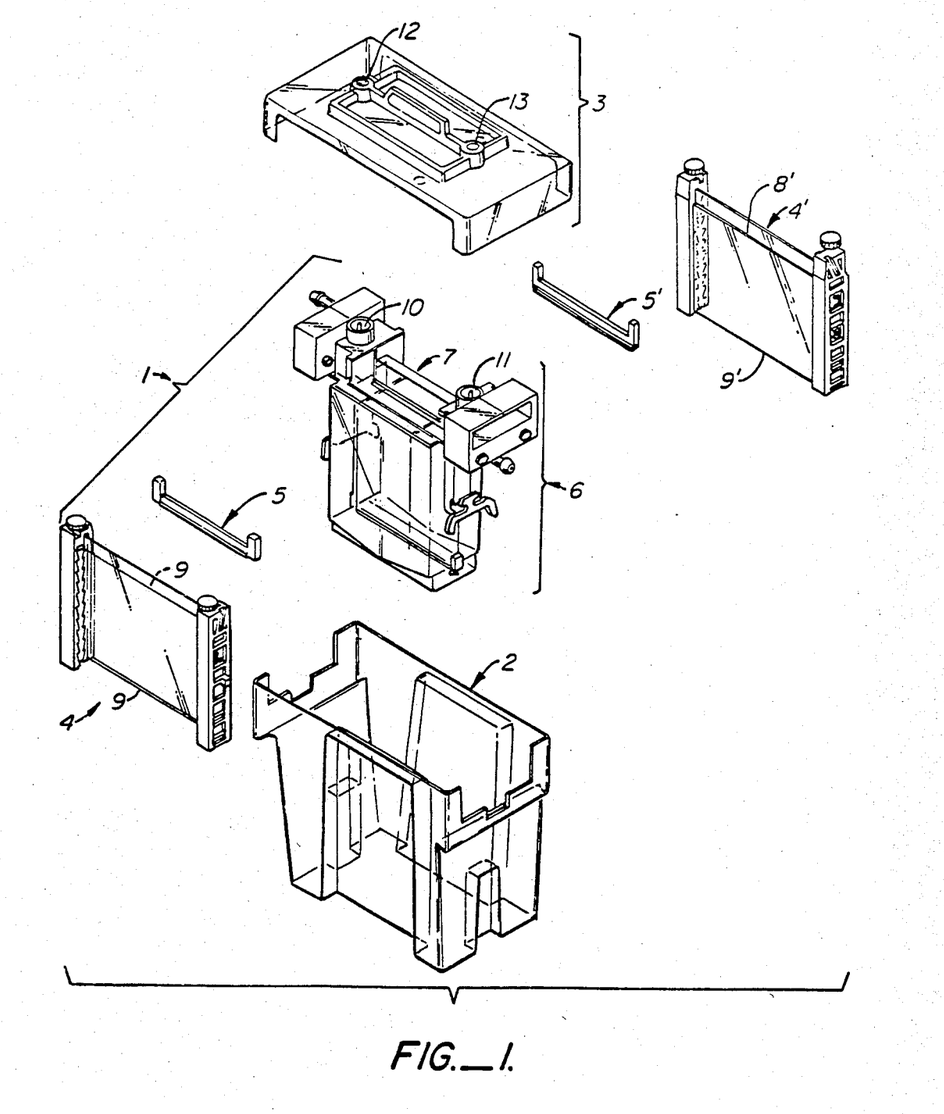
FIG. 1 is an exploded perspective view of an illustration of the apparatus of the present invention as applied to a pair of slab gels, together with a lower buffer chamber and lid.

The descriptive details which follow will be best understood by first examining FIG. 1, which is an exploded perspective view of an illustrative embodiment of the invention as applied to slab gels in a typical environment. In this figure, the apparatus of the present invention 1 appears in combination with further accessories—a tank 2 and a lid 3—similar to those typically used to complete an electrophoresis cell for a vertical slab gel.

The figure shows two gel slab enclosures 4 and 4' in the form of plate assemblies, and two gaskets 5 and 5' which combine with a structure 6 which incorporates a U-shaped frame 7 mounted above a coolant chamber. When these parts are joined together, an upper buffer chamber is formed and the upper edges 8 and 8' of the gel slabs are sealed into the interior of the chamber. This symmetrical arrangement is preferred by virtue of its efficiency. The essence of the invention, however, is the combination of at least one gel plate assembly and gasket with the frame.

The tank 2 is intended to contain a lower buffer solution. When the combined plate assemblies and frame are placed inside the tank, the lower edges 9 and 9' of both gel slabs are immersed in the lower buffer solution, whose level is kept well beneath the lowest point of the upper buffer chamber. The shape of the tank as shown is designed to minimize the volume of the lower buffer solution required, yet accommodate the entire assembly of gels, plates and frame. Alternatively, the tank may be sized to accommodate a plurality of such assemblies, providing a single body of lower buffer solution common to all gels.

The lid 3 protects the user by shielding him from the electrified solution in the upper buffer chamber, yet permitting access to the electrical terminals 10 and 11 through passages 12 and 13.

The remaining Figures address each of the components of the claimed apparatus 1 in detail.

Figure 2:
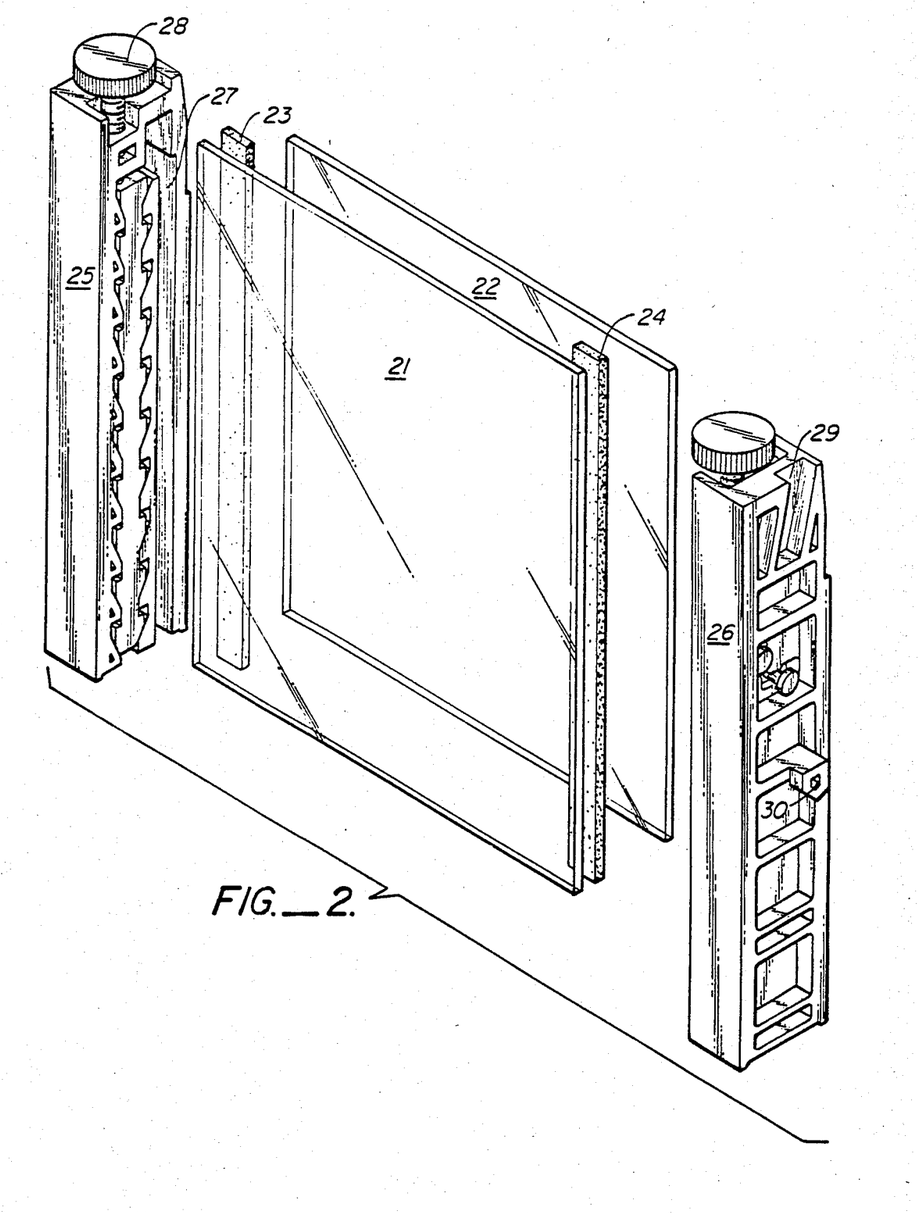
FIG. 2 is an exploded perspective view of the slab gel plate assembly shown as one of the components in FIG. 1.

FIG. 2 is an exploded view of the gel plate assembly 4 of FIG. 1. This figure shows a pair of gel support plates 21 and 22 of unequal height and liquid-retaining spacers 23 and 24 to define a volume between the plates for containing the gel. The plates and spacers form a lateral enclosure around the gel, leaving only the upper and lower edges of the gel exposed. The portion of the higher plate 21 which extends above the upper edge of the lower plate 22 forms a liquid-retaining wall which forms one side of the upper buffer chamber when the assembly is joined to the U-shaped frame 7 shown in FIG. 1. The gel is cast in this assembly prior to attachment of the assembly to the remainder of the apparatus. Additional support plates and spacers may be used for multi-layered gel sandwiches, with a slab gel between each adjacent pair of plates. Only the outermost plate will be raised, however, so that the buffer solution will have full access to the top edge of each gel.

Gel plate assemblies which are preferred for use in the present invention are those in which the upper edges of both plates are straight as shown in the figure, since as indicated above such plates are generally easier to make and less prone to breakage, particularly if they are glass. A notched plate can also be used as the shorter plate, however, as in the Studier and Hoefer designs. The choice between notched or straight-edge plates will require appropriate adjustments to the shape of the gasket for sealing purposes, as described in more detail below.

Plate 21 is the taller of the two, and the gel once cast extends only as high as the upper edge of the shorter plate. Although the spacers shown in the Figure are the same height as the taller plate, this is primarily a matter of convenience. In general, the spacers need only extend as high as the gel itself. The extra height, however, helps to facilitate the alignment of the pieces prior to tightening down on the clamps, placing the gel-forming fluid in the space between the plates and solidifying it into a gel.

The plates and spacers may be formed from any material which is electrically nonconducting and which is inert to the gel, the sample mixture containing the species to be separated, and the buffer solutions. It is preferred to use plates which are transparent so that the progress of the separation and the condition of the other cell components can be monitored while the cell is in use. Glass is a particularly convenient material for this purpose. Frosted glass may be substituted for clear glass when low percent gels or other gels which slide easily are used, since the frosted surface will promote adherence of the gel and thereby inhibit slippage.

The plates are held together along their vertical edges by end clamps 25 and 26. The latter are mirror images of each other and are preferably designed to provide a uniform pressure along the entire length of the plates, thus enhancing the seal and minimizing the danger of breakage. The clamps are generally characterized by an inside groove 27 of a width which is adjustable by a screw 28, and an outer surface having an angled open channel 29 at the top and a protruding lug 30 near the bottom which can be laterally gripped. The channel and lug are functional in securing the plate assembly to the upper buffer chamber frame by mating with structural members on the frame, as shown in the subsequent drawings and described in detail below.

Once the parts shown in FIG. 2 are assembled, the gel is cast according to known procedures, generally on a casting stand. A row of sample pockets or wells may be formed in the top of the gel slab according to known techniques, such as by the insertion of a combshaped device into the top of the gel space before the gel is hardened. Alternatively, for two-dimensional electrophoresis, a tube gel containing a sample already separated into components along the tube axis is laid lengthwise along the top edge of the slab for electrophoretic transfer in the transverse direction into the slab. The upper edge of the lower plate 22 may be bevelled outward to form a trough to hold the tube gel in place.

Figure 3A:
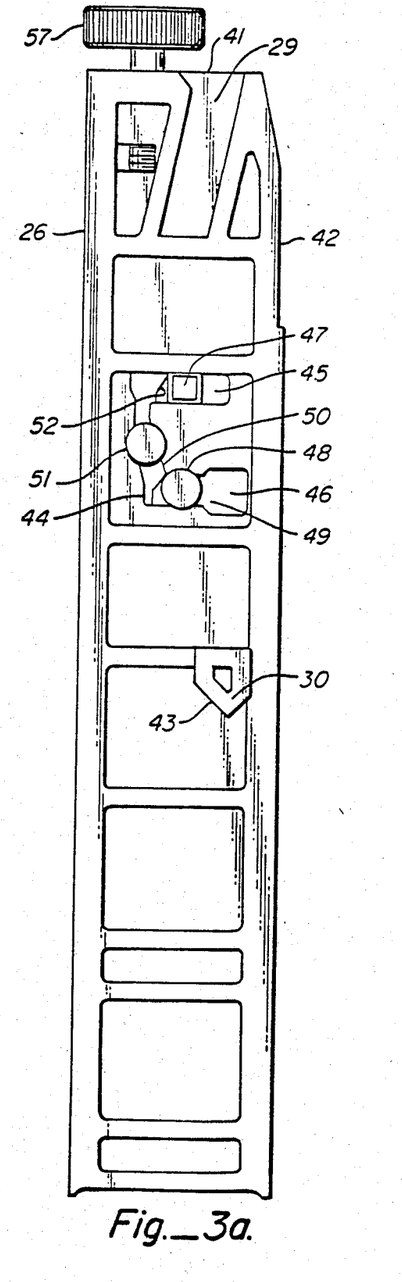
FIG. 3a is an end view and FIG. 3b is a view of the inner surface facing the gel support plates.
Figure 3B:
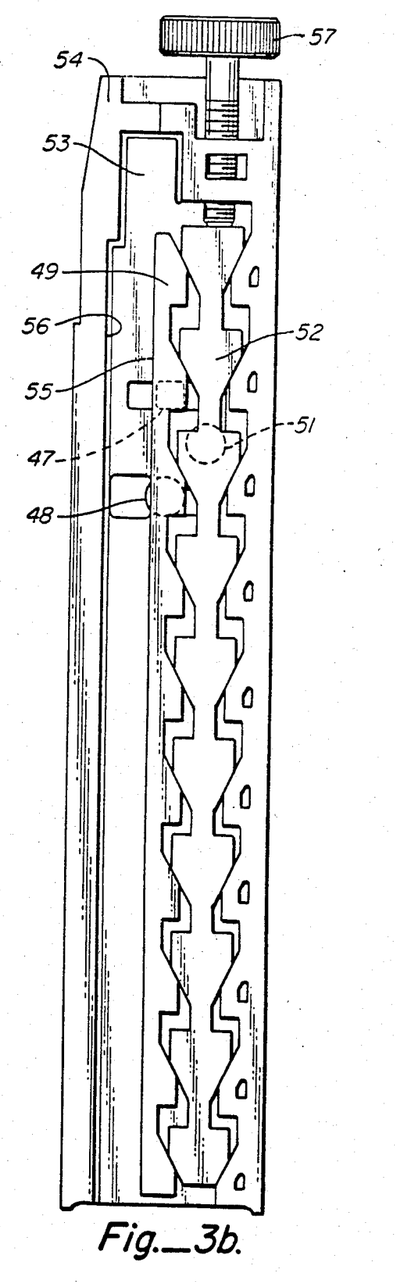

FIGS. 3a and 3b provide a closer look at the right end clamp 26 shown in FIG. 2.

FIG. 3a shows the outer surface of the clamp, with an angled open channel 29 beginning at the upper edge 41 of the clamp and extending downward at an acute angle away from the side edge 42 which is on the same side of the clamp as the shorter support plate (plate 22 in FIG. 2). This channel operates as a slide for a support pin on the buffer chamber frame, as will be described in more detail below. Alternatively, the pin and channel may be reversed, the former on the clamp and the latter on the buffer chamber frame. The arrangement shown in the drawings, however, is preferred.

A protruding lug 30 is positioned below the channel. The lug protrudes outward from the clamp surface and is shaped and positioned so that it can be gripped by a releasable catch on the buffer chamber frame, the catch bearing on the lug in both the lateral and upward direction. It is particularly convenient to use a V-shaped lug as indicated, the securing force being incident on the left side 43 of the V. As in the case of the pin and guide, the lug and catch may also be reversed, although the arrangement shown is preferred. The catch is described in detail below, in connection with FIG. 4c.

The remaining features of the end clamp relate to the means in which the clamp functions to hold the gel sandwich together. In this respect, the functional features are merely an illustrative embodiment; other designs which function similarly can also be used.

An elongated hole 44 passes completely through the clamp. The hole consists of two parallel horizontal portions 45 and 46, connected by a slanted portion 50. The horizontal portions are arranged to accommodate pins 47 and 48 respectively which project from a movable bar 49 on the other side of the clamp, restricting the movement of the bar to the lateral direction. The slanted portion of the hole accommodates pin 51 projecting from a second bar 52, also located on the other side of the clamp, restricting its motion to the diagonal direction. Pins 48 and 51 extend forward beyond the edge of the hole, and have widened heads to hold each bar in place against the clamp housing. Both bars are best seen in FIG. 3b, from which the significance of their motion is readily understood.

FIG. 3b shows the reverse side of the same clamp. The clamp consists of a housing 54 with a recess 53 containing both movable bars 49 and 52. On the first bar 49, the left side 55 is straight and parallel to the opposing inner wall 56 of the recess, thus defining a groove for receiving the edges of the gel plate sandwich. The right side has a series of angled surfaces which mirror similarly angled surfaces on the other inner wall of the recess, thereby defining a vertical row of wedge-shaped spaces. The second bar 52 has angled surfaces on both sides complementary to those of the first bar and the housing. By bearing down on the second bar, the first bar is urged to the left providing uniform pressure against the nearest glass plate in the groove. The pressure is governed by the screw 57 which forces the second bar downward. Due to the angle of the slanted portion 50 of the guide slot, the motion of the second bar is limited to a direction parallel to the angled surfaces on the inner wall of the housing recess.

Figure 4A:
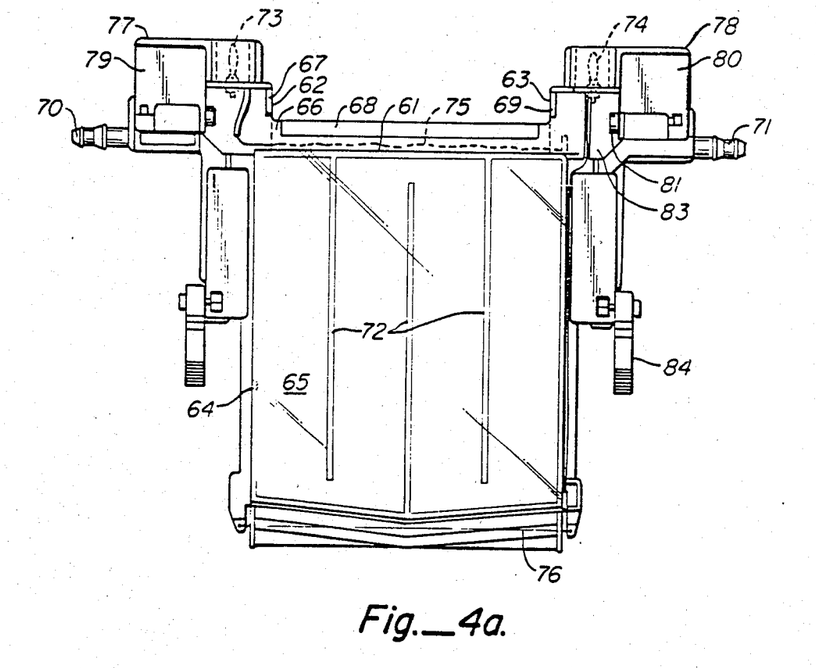
FIG. 4a is a front view.
Figure 4B:
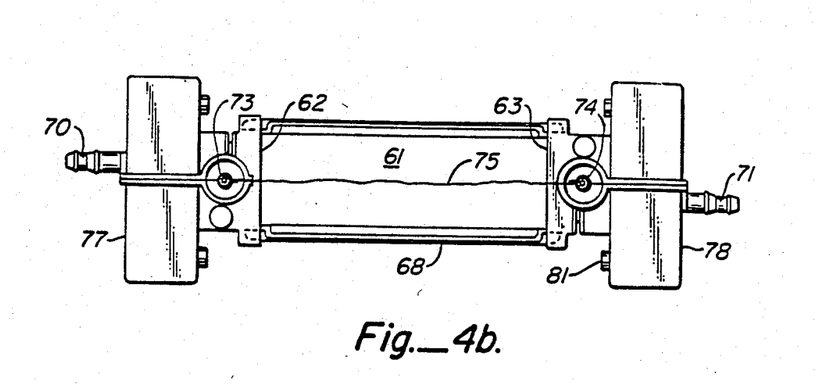
FIG. 4b is a top view.
Figure 4C:
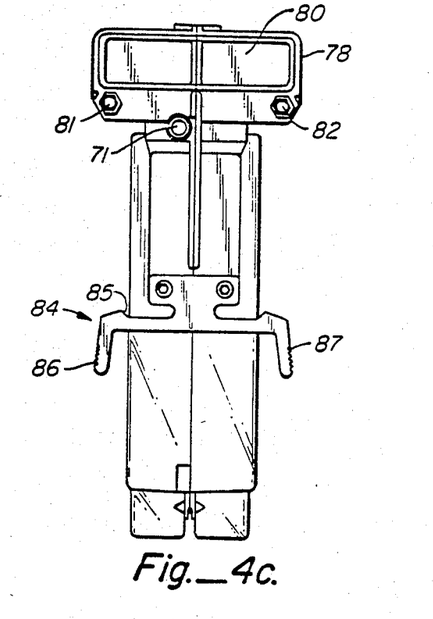
FIG. 4c is a side view.

FIGS. 4a, 4b and 4c offer a detailed depiction of the upper buffer chamber frame and coolant chamber combination 6 of FIG. 1.

The upper buffer chamber frame itself is defined by a floor 61 and end walls 62 and 63 in the shape of a U. In the embodiment shown, the floor 61 also serves as the roof of a coolant chamber 64 located directly below the upper buffer chamber frame. The coolant chamber has a flat heat transfer surface 65 of dimensions similar to those of the gel slab. In assembly, the heat transfer surface 65 and the shorter slab support plate are in contact, with heat exchange occurring in the direction perpendicular to the plane of the gel slab.

The upper buffer chamber also has short side walls 66 which, together with the edges of the end walls 62 and 63 form a flat U-shaped surface against which a U-shaped gasket (described below) is compressed. Guides 67, 68 and 69 protrude from this surface to facilitate the placement of the gasket.

Coolant flows through the coolant chamber by way of inlet and outlet lines 70 and 71, respectively. A series of baffles 72 in the interior of the chamber serve to distribute the flow of the coolant medium and enhance the uniformity of cooling over the entire heat transfer surface 65.

The electrical connections for applying a voltage across the gel slabs and thereby running a current through the cell are shown as standard "banana"-type plugs 73 and 74, designed for connection in a standard manner to an external power source. One of the plugs 73 connects to a wire 75 in the upper buffer chamber, while the other 74 connected to a wire 76 below the coolant chamber. When the assembly is placed in a tank 2 as shown in FIG. 1, the lower wire 76 will be immersed in a lower buffer solution. The lower end of the coolant chamber is V-shaped to allow bubbles generated by the passage of a current through the wire to escape without being entrapped under the gel plate assemblies.

The frame also has support members 77 and 78 in the form of shoulders extending outward from each side, with recesses 79 and 80 to enable the user to grasp the entire assembly when inserting it into or removing it from the tank. Behind each recess is a pair of pins 81 and 82, protruding inward into an open space 83. Each pin is sized and positioned to mate with an angled open channel 29 of an end clamp (as shown in FIG. 3a), while the open space accommodates the upper forward corner of the end clamp. To attach a plate assembly to one side of the frame, the upper edge of the assembly is inserted into the spaces 83 so that each of the two pins on that side of the frame slips into a corresponding end clamp channel through the opening at the top of the channel. The entire assembly is then slid upward at an angle, with the pins traveling along the channels. At the end of the travel, the shorter of the two gel support plates is pressed against a gasket (not shown in FIG. 4a) which thereby seals off the upper buffer chamber, while the taller support plate extends well above the upper edge of the side wall. The gasket is shown in FIGS. 5a, b, and c, described below.

Below each shoulder is a latch 84 which is shaped and positioned to mate with the lug 30 (see FIG. 3a) which protrudes outward from the end surface of the end clamp. The angled surface 85 on the latch mates with the similarly angled surface 43 on the lug to function as a catch which grips the lug and forces the plate assembly up against the coolant chamber and gasket. As shown in FIG. 4c, the latch is symmetrical to accommodate two gel slabs, one on each side of the coolant chamber. The latch has tabs 86 and 87 extending downward which can be squeezed together to open the catches and release the plate assembly. The latch is therefore constructed of a material which is slightly deformable yet resilient and sufficiently stiff to hold the parts securely together.

Figure 5A:
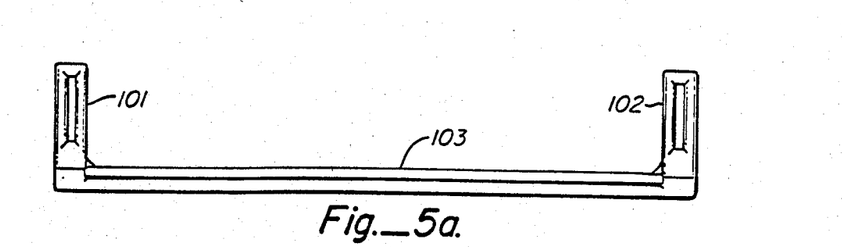
FIGS. 5a, 5b and 5c are a front view, top view and side view, respectively, of the gasket appearing in FIG. 1.
Figure 5B:
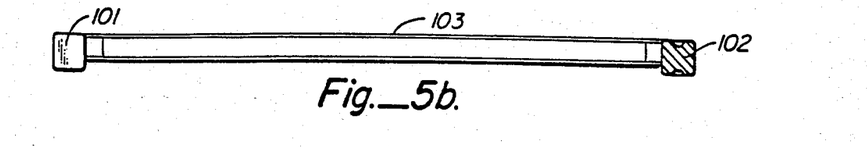
Figure 5C:
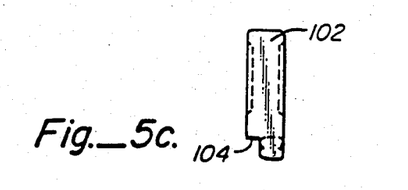

FIGS. 5a, 5b and 5c offer a detailed depiction of the gasket 5 shown in FIG. 1. The gasket is generally U-shaped with two vertical portions 101 and 102, separated by a horizontal portion 103. The total width of the gasket is approximately equal to the width of the gel support plates, and the horizontal portion is preferably at least as wide as the gel itself. For plate assemblies where the shorter plate has a central elongated notch, a gasket which is flat on both sides will suffice. For plate assemblies where both plates have straight upper edges, the gasket will have a stepwise profile as shown in FIG. 5c, with an inverted shoulder 104. The latter fits over the top edge of the shorter plate, with the vertical portions extending forward far enough to contact either the exposed inner surface of the taller plate or the exposed surfaces of the spacers, depending on whether or not the spacers extend upward to the full height of the taller plate. In either case, the vertical and horizontal portions of the gasket will provide a lateral and a horizontal seal respectively for the space above the upper edge of the gel.

The symmetrical arrangement shown requires a plate assembly on each side to complete the four vertical walls of the upper buffer solution chamber. When only one gel slab has been prepared for electrophoresis, a solid dummy plate with the same dimensions at the assembled support plates (including stepwise profile) can be used in place of the second plate assembly. As mentioned earlier, the symmetrical arrangement shown is but one embodiment of the invention. Asymmetrical structures which accommodate only one gel plate assembly are also contemplated, provided that they contain the mating, securing and sealing features characteristic of the invention as a whole.

Figure 6:
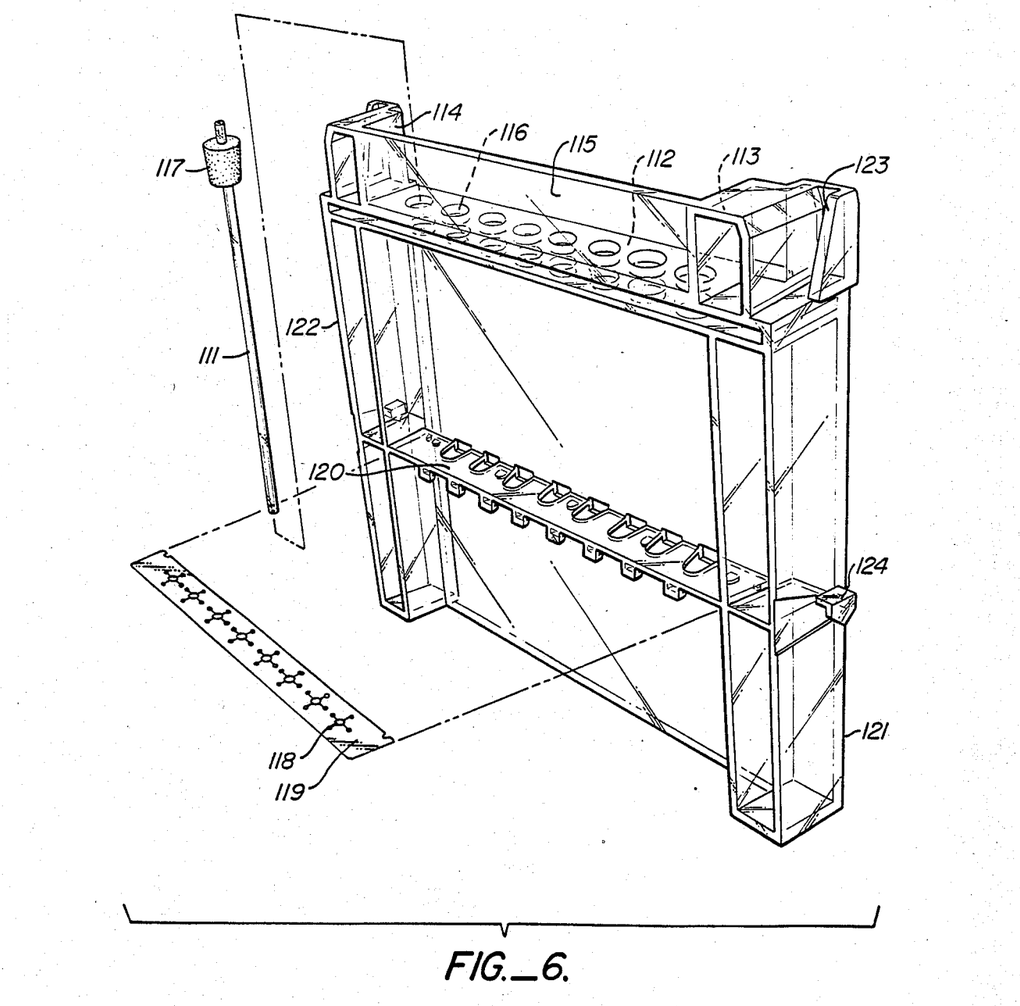
FIG. 6 is an exploded perspective view of a gel enclosure for tube gels, designed to mate with the upper buffer chamber support frame shown in FIGS. 4a, 4b and 4c in place of the slab gel plate assembly shown in FIG. 2.

FIG. 6 illustrates a tube gel enclosure 110 intended for mounting to one side of the U-shaped buffer chamber frame and coolant chamber assembly of FIGS. 4a, 4b and 4c, as a substitute for the slab gel plate assembly of FIG. 2. The enclosure consists of a hollow tube 111 for retaining each tube gel and a U-shaped rack defined by a horizontal portion 112 and a pair of upright legs 113 and 114. The rack is enclosed at one side by a liquid-retaining wall 115 which corresponds in function to the higher gel support plate 21 of the slab gel plate assembly shown in FIG. 2, thus forming one side of the upper buffer chamber when the rack is joined to the U-shaped frame 7 shown in FIG. 1.

The horizontal portion 112 of the rack has a series of holes 116, one for each tube 111. A grommet 117 is placed around each tube to seal the tube into its respective hole. The tubes are positioned in the holes so that their upper exposed ends terminate below the upper edge of the liquid-retaining wall 115, enabling the wall to retain buffer solution at a sufficient depth to immerse the gel ends. Holes which are not in use are sealed by stoppers (not shown). The lower ends of the tubes are passed through guide holes 118 in a strip of flexible resilient material 119 which provides lateral stability to the tubes. The strip is supported in a secondary rack 120 directly below the horizontal portion 112 of the U-shaped rack.

Support members 121 and 122 extend downward from each leg of the U-shaped rack to support the secondary rack 120, an angled guide 123 and a protruding lug 124. The angled guide 123 corresponds to the angled channel 29 of the end clamp shown in FIG. 3a used in the gel slab assembly, and mates with pin 81 of FIG. 4 in the same manner. The lug 124 is similar to the corresponding lug 30 on the end clamp, mating in the same manner with the latch 84 on the side of the coolant chamber. These features permit the substitution of the tube gel enclosure for the slab gel plate assembly shown in FIG. 2, securing it to the upper buffer chamber frame and coolant chamber in identical fashion using an appropriately shaped gasket (i.e., either stepped or flat).

The foregoing description is intended primarily for purposes of illustration. The invention as a whole is not intended to be limited to the particular structural or operational features described above. Numerous modifications and variations, still falling within the spirit of the scope of the invention, will be readily apparent to those skilled in the art.

What is claimed is:

1. Apparatus for performing electrophoresis across at least one vertical gel, comprising:
    a lateral enclosure for said vertical gel open at the top and bottom and extending upward at one side to a height sufficient to form a liquid-retaining wall;
    a U-shaped frame combinable with one said lateral enclosure at each side thereof to form a liquid-retaining receptable defined by said U-shaped frame and one said liquid-retaining wall from each said lateral enclosure, the interior thereof communicating with the open top of each said lateral enclosure;
    a pin on one of said lateral enclosure and said U-shaped frame and a guide for said pin on the other of said lateral enclosure and said U-shaped frame, said pin and guide in cooperating relationship to slide said lateral enclosure into pivotal contact with said U-shaped frame; and
    a lug on one of said lateral enclosure and said U-shaped frame and a releasable catch for said lug on the other of said lateral enclosure and said U-shaped frame to secure said lateral enclosure against said U-shaped frame.

2. Apparatus according to claim 1 in which said pin is laterally extending and said guide is angled inward toward the tops of said lateral enclosure and U-shaped frame.

3. Apparatus according to claim 1 in which one pin and said guide are at one leg of said U toward the tops of said lateral enclosure and said U-shaped frame, and said lug and said releasable catch are below said pin and guide; said apparatus further comprising a second pin and a second guide at the other leg of said U toward the tops of said lateral enclosure and said U-shaped frame, and a second lug and releasable catch below said second pin and said second guide; said pins and said guides together providing a hinge-type connection between said lateral enclosure and said U-shaped frame.

4. Apparatus according to claim 1 further comprising a coolant chamber extending downward from the base of said U-shaped frame.

5. Apparatus according to claim 1 further comprising a coolant chamber extending downward from the base of said U-shaped frame, a first exposed electric wire inside said U-shaped frame and a second exposed electric wire beneath said coolant chamber, and means for applying a voltage between said wires.

6. Apparatus according to claim 1 in which said gel is a slab gel and said lateral enclosure is a plurality of plates secured together by an end clamp at each side edge thereof with liquid-retaining lateral spacers between each adjacent pair of plates to define an open space sufficient to accommodate said slab gel, the outermost plate of said plurality of plates having an upper edge extending above at least the central portions of the upper edges of the remaining plates of said plurality of plates to form said liquid-retaining wall.

7. Apparatus according to claim 1 in which:
said gel is a slab gel and said lateral enclosure is a plurality of plates secured together by a pair of end clamps, one at each side edge thereof, with liquid-retaining lateral spacers between each adjacent pair of plates to define an open space sufficient to accommodate one said slab gel, the outermost plate of said plurality of plates having an upper edge extending above at least the central portions of the upper edges of the remaining plates of said plurality of plates to form said liquid-retaining wall;
said pin extends inward from a support member extending laterally from a first leg of said U-shaped frame, and said guide is formed in the outer surface of a first end clamp of said pair of end clamps, said guide being comprised of an angled groove open to the top of said first end clamp; and
said lug protrudes laterally from said first end clamp below said angled groove, and said releasable catch is mounted below said first leg of said U-shaped frame to engage said lug.

8. Apparatus according to claim 1 in which said gel is a plurality of tube gels, and said lateral enclosure is comprised of a plurality of hollow tubes open at both ends for receiving said tube gels and a U-shaped rack to mate with said U-shaped frame in liquid-tight manner, the horizontal portion of said U-shaped rack having a hold to receive each tube of said plurality of tubes in liquid-tight manner, and said U-shaped rack enclosed at one side with a liquid-retaining wall of sufficient height to retain sufficient liquid to immerse the upper ends of the tubes of said plurality of tubes when said U-shaped rack is secured to said U-shaped frame.

9. Apparatus according to claim 1 in which said gel is a plurality of tube gels, and said lateral enclosure is comprised of a plurality of hollow tubes open at both ends for receiving said tube gels, and a U-shaped rack to mate with said U-shaped frame in liquid-tight manner, the horizontal portion of said U-shaped rack having first and second legs and a hole to receive each tube of said plurality of tubes in liquid-tight manner, said U-shaped rack being enclosed at one side with a liquid-retaining wall of sufficient height to retain sufficient liquid to immerse the upper ends of the tubes of said plurality of tubes when said U-shaped rack is secured to said U-shaped frame; said apparatus further comprising first and second support members extending downward from the ends of said U-shaped rack, said lug protruding laterally from said first support member; and said guide is formed in the lateral surface of said first leg of said U-shaped rack, said guide being comprised of an angled track extending downward from the top of said first leg for engaging said pin; said apparatus further comprising a second lug protruding laterally from said second support member, a second releasable catch for said second lug, a second pin, and a second guide in the lateral surface of said second leg, said second guide being comprised of an angled track extending downward from the top of said second leg for engaging said second pin.

10. Apparatus for performing electrophoresis in a vertical gel slab held between a pair of flat substantially rectangular support plates of which at least the central portions of the upper edges of each are at unequal heights, said apparatus comprising:
first and second elongate end clamps for securing said support plates together along their vertical edges with said gel slab therebetween to form a plate assembly, the end surfaces of said first and second elongate end clamps having first and second open channels respectively extending from the upper edges thereof downward at an acute angle away from the shorter of said support plates and first and second laterally protruding lugs below said first and second open channels respectively;
a frame for vertically supporting said plate assembly, said frame containing a horizontal surface intersecting a pair of vertical surfaces to form the bottom and end walls respectively of a substantially rectangular upper buffer solution chamber one side wall of which is defined by the exposed portion of the inner surface of the taller of said support plates;
a U-shaped gasket having two vertical portions connected by a horizontal portion such that, when said gasket is compressed between said plate assembly and said frame, said vertical portions laterally seal the portion of said plate assembly extending above said gel slab against said vertical surfaces of said frame and said horizontal portion seals the shorter of said support plates against said horizontal surface of said frame;
first and second pins mounted in said frame to mate with said first and second open channels respectively and to guide said plate assembly into position against said frame; and
first and second releasable catches mounted on said frame to grip said first and second laterally protruding lugs respectively and secure said plate assembly to said frame with said Ushaped gasket compressed therebetween.

11. Apparatus according to claim 10 in which said support plates have straight upper edges, and said vertical portions of said U-shaped gasket extend forward from said horizontal portion over the upper edge of the shorter of said support plates to seal the taller of said support plates against said vertical surfaces of said frame.

12. Apparatus according to claim 10 in which said support plates have straight upper edges and the distance between said support plates establishing the thickness of said gel slab is defined by a pair of flat elongate spacers held between said support plates along the vertical edges thereof and extending substantially the full height of the taller of said support plates, and said vertical portions of said U-shaped gasket extend forward from said horizontal portion over the upper edge of the shorter of said support plates to seal the exposed surfaces of said flat elongate spacers against said vertical surfaces of said frame.

13. Apparatus according to claim 10 further comprising third and fourth elongate end clamps, a second U-shaped gasket, third and fourth pins and third and fourth releasable catches to secure to said frame a second plate assembly substantially identical to and facing the first, whereby the exposed portions of the inner surfaces of the taller support plate of each said plate assembly define opposing side walls of said upper buffer solution chamber.

14. Apparatus according to claim 10 in which said frame further contains a coolant chamber below said horizontal surface and means for passing coolant therethrough, said coolant chamber having a flat heat exchange surface in contact with the shorter of said support plates to control the temperature of said gel slab.

15. Apparatus according to claim 10 in which each of said first and second elongate end clamps comprises a housing having an elongate recess on the side facing said support plates, a laterally movable elongate bar within said elongate recess, a wall of said elongate recess and one side of said laterally movable elongate bar defining a groove for receiving the vertical edges of said support plates with said gel slab therebetween, and said clamps further comprising means for urging said laterally movable elongate bar toward said wall with substantially constant pressure along the entire length of said laterally movable elongate bar.

16. Apparatus for performing simultaneous electrophoresis in a pair of vertical gel slabs, each said slab held between a pair of flat rectangular support plates with straight upper edges of unequal heights and each said slab having a thickness defined by flat elongate spacers between said plates along the vertical edges thereof, said apparatus comprising:

a pair of plate assemblies, each said assembly containing first and second elongate end clamps for securing said flat rectangular support plates together with said flat elongate spacers therebetween, the end surfaces of said first and second elongate end clamps having first and second open channels respectively extending from the upper edges thereof downward at an acute angle away from the shorter of said flat rectangular support plates and first and second laterally protruding lugs below said first and second open channels respectively, said plate assemblies arranged in parallel, opposing relation with the shorter of said flat rectangular support plates facing each other;

a frame for vertically supporting said pair of plate assemblies, said frame containing a horizontal surface intersecting a pair of opposed vertical surfaces to form the bottom and end walls respectively of a substantially rectangular upper buffer solution chamber each side wall of which is defined by the portion of the taller of each said pair of flat rectangular support plates extending above the upper edge of the shorter of said pair of flat rectangular support plates, said frame further containing a coolant chamber below said horizontal surface and means for passing coolant therethrough, said coolant chamber having a pair of opposing flat heat exchange surfaces each adapted to contact the shorter of said pair of flat rectangular support plates of each plate assembly to control the temperature of each said gel slab;

a pair of U-shaped gaskets each having two vertical portions connected by a horizontal portion, said vertical portions extending beyond one side of said horizontal portion over the upper edge of the shorter of said support plates such that, when each said U-shaped gasket is compressed between one of said plate assemblies and said frame, said vertical portions laterally seal the portion of the taller of said pair of flat rectangular support plates extending above the upper edge of the shorter of said pair of flat rectangular support plates against said opposed vertical surfaces of said frame while said horizontal portion seals the shorter of said pair of flat rectangular support plates against said horizontal surface of said frame;

two pairs of opposing pins mounted in said frame, one said pair on each side thereof, each said pair adapted to mate with said first and second open channels on one of said pair of plate assemblies and to guide said one plate assembly into position against said frame; and two pairs of releasable catches mounted on said frame, one said pair on each side thereof, each said pair adapted to grip said first and second laterally protruding lugs on one of said pair of plate assemblies and thereby secure said one plate assembly to said frame with one of said pair of U-shaped gaskets compressed therebetween.

17. Apparatus according to claim 16 further comprising a first exposed electric wire in said substantially rectangular upper buffer solution chamber extending substantially the full length thereof, a second exposed electric wire beneath said coolant chamber extending substantially the full length thereof, and means for applying a voltage between said wires.

18. Apparatus according to claim 17 further comprising a tank sized to accommodate said frame with said pair of plate assemblies attached and adapted to retain a lower buffer solution at sufficient depth to fully immerse both said second exposed electric wire and the lower edge of each of said pair of vertical gel slabs.

* * * * *